(12) United States Patent
Dey et al.

(10) Patent No.: US 7,005,429 B2
(45) Date of Patent: Feb. 28, 2006

(54) METHOD OF TREATING ESTROGEN RECEPTOR POSITIVE CARCINOMA WITH 17 α-DIHYDROEQUILIN

(75) Inventors: Michael S. Dey, Grand Isle, VT (US); Frederick J. Bex, Delaware, PA (US); Alan Corbin, Delaware, PA (US)

(73) Assignee: Wyeth, Madison, NJ (US)

( * ) Notice: Subject to any disclaimer, the term of this patent is extended or adjusted under 35 U.S.C. 154(b) by 744 days.

(21) Appl. No.: 09/962,352

(22) Filed: Sep. 26, 2001

(65) Prior Publication Data

US 2002/0035101 A1 Mar. 21, 2002

Related U.S. Application Data

(63) Continuation of application No. 07/973,930, filed on Nov. 10, 1992, now Pat. No. 6,342,491, which is a continuation of application No. 07/703,446, filed on May 21, 1991, now abandoned.

(51) Int. Cl.
    *A61K 31/56* (2006.01)

(52) U.S. Cl. ..................................................... 514/182
(58) Field of Classification Search ................. 514/182
    See application file for complete search history.

(56) References Cited

PUBLICATIONS

PDR, 43ed,(1989), pp. 2355-2358.*
Escher et al., Current Views on the Management of Metastatic Mammary Carcinoma,: *M. Clin., North America* 45:613-625 (1961).
Segaloff and Ochsner, "Results of Studies of the Cooperative Breast Cancer Group–1961–63$^{1.2}$," *Cancer Cehmotherapy Reports*, 41:1-24 (1964).
Segaloff and Ochsner, "Progress Report: Results of Studies of the Cooperative Breast Cancer Group–1956–60$^{1.2}$," Cancer Chemotherapy Reports, 11:109-141 (1961).
"Current Status of Hormone Therapy of Advanced Mammary Cancer," *Journal of American Medical Assoc.* 146(5):471-477 (Jun. 1951).
Lewison et al., "Tracer Studies of Radioactive Sodium Estrone Sulfate (S$^{35}$) in Cases of Advanced Breast Cancer," *Cancer*. 537-548 (May 1951).
McCormick, "Benign and Malignant Diseases of the Breast," *Journal of American Medical Association* 146(5):461-464 (Jun. 1951).
Taylor et al., "Hormones in Breast Metastasis Therapy," *M. Clin. North American*, 35:51-61 (1951).
Griboff, "The Rational and Clinical Use of Steroid Hormones in Cancer," *A.M.A. Archives of Internal Medicine* 89:635-685 (Apr. 1952).
Woodward, et al., "Changes in the Blood Chemistry of Patients with Disseminated Carcinoma of the Breast During Endocrine Therapy," *Cancer* 74(4):744-757 (Jul. 1954).
"Questions and Answers," GP 7(1):82-84 (Jan. 1954).
Taylor, "Hormonal Modification in the Treatment of Disseminated Cancer of the Breast," *American Journal of Medicine* 21:688-696 (Nov. 1956).
Kennedy et al., "Surgery as an Adjunct to Hormone Therapy of Breast Cancer," *Cancer* 10(5):1055-1075 (Sep.-Oct. 1957).
Mustacchi et al., Frequency of Cancer in Estrogen-Treated Osteoporotic Women, in Segaloff, A.: *Breat Cancer, the Second Biennial Louisiana Cancer Conference, New Orleans, Jan. 22-23, 1958, St. Louis*, The C.V. Mosby Company, pp 163-169. (1958).
Block, "Endocrine Treatment of Advanced Mammary Cancer," *GP* 20(4), 85-96 (Oct. 1959).
Lemon, "Prednisone Therapy of Advanced Mammary Cancer," *Cancer* 12(1) 93-107 (Jan.-Feb. 1959).
Baker et al., "Hormonal Treatment of Metastatic Carcinoma of the Breast," *American Journal of Surgery* 99:538-543 (Apr. 1960).
Council on Drugs: "Androgens and Estrogens in the Treatment of Disseminated Mammary Carcinoma," *Journal of American Medical Association*, 172 (12):1271-1283 (1960).
Kelley, "Medical Aspects of the Hormonal Treatment of Cancer," *Modern Medicine* 28:117-126 (Apr. 1960).
Whitney, "The Endocrine Palliation of the Breast Cancer Patient," *The Journal of the Maine Medical Association*, 51:433-438 (Dec. 1960).
Kennedy, "Massive Estrogen Administration in Premonopausal Women with Advanced Breast Cancer," *Cancer Chemotherapy Reports*, 16:283-284 (Feb. 1962).
Kennedy, "Massive Estrogen Administration in Premonopausal Women with Advanced Breast Cancer," *Cancer* 15(3): 641-648 (May-Jun. 1962).
Wilson, "The Roles of Estrogen and Progesterone in Breast and Genital Cancer," *Journal of American Medical Association*, 182 (4):327-331 (Oct. 1962).
Hertz et al., Administration of Massive Dosage of Estrogen to Breast and Prostatic Cancer Patients; Blood Levels Attained,: *Ciba Foundation Colloquia*, Endocrinology, 1:157:169 (1952).
Rukes and Galante, "Palliative Treatment of Metastatic Cancer of the Breast," *GP*, 10(4), 83-93 (Oct. 1954).

(Continued)

*Primary Examiner*—Rebecca Cook
(74) *Attorney, Agent, or Firm*—Finnegan, Henderson, Farabow, Garrett & Dunner, L.L.P.

(57) ABSTRACT

This invention provides a method of treating estrogen receptor positive carcinoma in a mammal in need thereof which comprises administering an antineoplastic amount of 17(α-dihydroequilin or a mammalian metabolic conjugate thereof orally, parenterally, transdermally, topically, rectally, intravaginally, intranasally, or intrabronchially. As such, the compounds of this invention are useful in treating estrogen receptor positive carcinomas such as carcinomas of the breast, uterus, ovary, fallopian tube, cervix, vagina, liver, pituitary, central nervous system, hypothalamus, bone, skin, kidney, urethra, prostate, and the like.

18 Claims, No Drawings

OTHER PUBLICATIONS

Adair et al., "The Use of Estrogens and Androgens in Advanced Mammary Cancer," *The Journal of American Medical Association*, 140(15), 1193–1200 (Aug. 1949).

Garland et al., "Roentgen and Steroid Hormone Therapy in Mammary Cancer Metastatic to Bone," *Journal of American Medical Association*, 144(2):997–1004 (Nov. 1950).

Kennedy and Nathanson, "Effects on Intensive Sex Steroid Hormone Therapy in Advanced Breast Cancer," *Journal of American Medical Association*, 152(12):1135–1141 (Jul. 1953).

Segaloff et al., "Hormonal Therapy in Cancer of the Breast," *Cancer*, 7(4):758–763 (Jul. 1954).

Kennedy et al., "Massive Estrogen Administration in Pre-monopausal Women with Advanced Breast Cancer," *Abstract of Proceedings of American Association of Cancer Research* 3:239 (#146) (1961).

Kaufman and Goodwin, "Cancer of the Prostate: Diagnosis and Treatment," *The Journal of American Geriatrics Society*, 4:296–305 (Mar. 1956).

Beck, "Hormonal Therapy of Carcinoma of the Breast," *Canadian Services Medical Journal*, 13:607–613 (Oct. 1957).

Stearns and Gordon, "Changes in Microscopic Pathology of Prostatic Carcinoma Following Estrogen Therapy and Surgery," *The Journal of Urology*, 79(2):333–338 (Feb. 1958).

Treves, The Treatment of Cancer, Espcecially Inoperalbe Cancer, of the Male Breast by Ablative Surgery (Orchiectomy, Adrenalectomy, and Hypophysectomy) and Hormone Therapy (Estrogens and Corticosteroids), *Cancer*, 12(4):820–832 (Jul.–Aug. 1959).

Reicher and Phillips, "Carcinoma of the Endometrium," *American Journal of Obstetrics and Gynecology*, 82(2):417–423 (Aug. 1961).

Urban, Current Trends in Breast Cancer Treatment, Part III, *New York State Journal of Medicine*, 61:3469–3477 (Oct. 1961).

Fergusson, "some Aspects of the Conservative Management of Prostatic Cancer," *Proceedings of the Royal Society of Medicine*, 56:81–88 (Feb. 1963).

Dederick et al., "Effect of Therapy upon Vaginal Smears in Breast Cancer patients," *Surgery, Gynecology & Obstetrics*, 118(5): 1019–1023 (May 1964).

Green et al., "Treatment of Advanced Carcinoma of the Breast," *The American Journal of Surgery, 108:107–121 (1964)*.

Rhoades, Progress in Management of Breast Cancer and Hypoestrogenism in the Aging Female, *American Geriatrics Society*, 12(9):877–880 (Sep. 1964).

Brendler and Prout, Jr., "A Cooperative Group Study of Prostatic Cancer: Stilbestrol Versus Placebo in Advanced Progressive Disease," *Cancer Chemotherapy Reports*, 16:323–328 (Feb. 1962).

The Veterans Administrative Co–Operative Urological Research Group, "Treatment and Survival of Patients with Cancer of the Prostate," *Surgery, Gynecology & Obstetrics*, 124(5): 1011–1017 (May 1967).

Whitmore, "Hormone Therapy in Prostatic Cancer," *The American Journal of Medicine*, 21:697–713 (Jul.–Dec. 1956).

Dorfman. Cahpters 4 & 5 in "Methods in Hormone Research—Steroidal Activity in Experimental Animals and Man," *Academic Press*, vol. 5, part C, New York (1966).

Holleb et al., "Cancer of Male Breast," *New York State Journal of Medicine*, 544–553 (Feb. 1968).

Kaufman et al., "Rebound Regression in Advanced Mammary Carcinoma," *Surgery, Gynecology & Obstetrics*, 113(5):635–640 (Nov. 1961).

Pfizer Spectrum: Mammary Cancer—Manipulations of the Milieu Interieur, *Journal of American Medical Associaton*, 153(8adv):21–23 (Oct. 1953).

Hall, "The Treatment of Inoperable Breast Cancer," *Medical Science*, pp 497–510 (Apr. 25, 1961).

Physicians' Desk Reference, 1989, pp. 2355–2358.

Pharmac. Ther. 25:127 (1984) J.A. Furr and V.C. Jordan.

Transcript of Ad Hoc Subcommittee of the Fertility & Maternal Health Drugs Adv. Committee, Conjugated Estrogens: *Bioequivalence Issues* p. 77–79 (publ. May 16, 1990).

* cited by examiner

METHOD OF TREATING ESTROGEN RECEPTOR POSITIVE CARCINOMA WITH 17 α-DIHYDROEQUILIN

RELATED APPLICATIONS

This application is a continuation of application Ser. No. 07/973,930, filed Nov. 10, 1992 now U.S. Pat. No. 6,342,491, which is a continuation of application Ser. No. 07/703,446, filed May 21, 1991 now abandoned, all of which are incorporated herein by reference.

BACKGROUND OF THE INVENTION

Estrogens have been shown to play an important role in the modulation of estrogen receptor positive breast carcinoma. Binding of endogenous estrogens, in particular 17β-estradiol ($E_2$), to the estrogen receptor has been linked to proliferation of the carcinoma cells, by causing the carcinoma cells to shift from the $G_1$ phase of the cell cycle to the S phase of the cell cycle. The $G_1$ stage of interphase is characterized by the cell being in a resting state, whereas it is during the S phase that the DNA synthesis necessary for cell survival and proliferation occurs.

Current trends in the treatment of estrogen receptor positive breast carcinoma are focused on the use of anti-estrogenic agents that prevent the binding of $E_2$ to the estrogen receptor. It has been postulated that an anti-estrogen may inhibit $E_2$ binding through competitive inhibition at the estrogen receptor or alternatively by binding to another site such as the anti-estrogen or calmodulin receptor, thereby preventing the binding of $E_2$ to the estrogen receptor. [V. C. Jordan, Pharmacol Rev 36: 245 (1984)]. In one study, approximately 60% of patients with estrogen receptor positive breast cancer (>10 femtomol/mg cytosol protein) responded to anti-estrogen therapy, whereas less than 10% of patients with estrogen receptor negative tumors (<10 femtomol/mg cytosol protein) responded. [J. L. Borgna, Biochem Pharmacol 31: 3187 (1982)]. Treatment of the estrogen receptor positive MCF-7 human breast cancer cells with tamoxifen [Z-1-(4β-dimethylaminoethoxyphenyl) 1,2-diphenyl but-1-ene citratel], a non-steroidal anti-estrogen, has been shown to inhibit cell $E_2$ stimulated cell growth by virtue of its ability to prevent the MCF-7 cells from entering the S phase of the cell cycle. [N. Brunner, Cancer Res 49: 1515 (1989)]. Chronic administration of tamoxifen (200 μg/day for 3 weeks) to mature female rats with dimethylbenzanthracene (DMBA) induced tumors prevents the accumulation of administered [$^3$H]-$E_2$ in uterine, vaginal, and mammary tumor tissue. [V. C. Jordan, J Endocr 68: 297 (1976)]. Presently, the treatment of choice for postmenopausal estrogen receptor positive breast carcinoma is tamoxifen. [V. C. Jordan, Pharmacol Rev 36: 245 (1984); A. U. Buzdar, Cancer 62: 2098, (1988); V. Hug, Br J Cancer 59: 421, (1989)].

Positive results with tamoxifen have been reported in several estrogen receptor positive ovarian carcinoma cell lines. [S. P. Langdon, J Endocrin 127/(Supp):119 (1990; G. dePalo, Acta Oncol 28: 163 (1989); K. R. Geisinger, Cancer 65: 1055 (1990); S. P. Langdon, Br J Cancer 62: 213 (1990)]. In addition, tamoxifen produced positive results in inhibiting the growth of several other estrogen receptor positive carcinomas including, DMBA-induced uterine adenocarcinoma in rats [S. Sekiya, J Obstet Gynaec Br Commonw 83: 183 (1976)]; Dunning R3327 rat prostrate adenocarcinoma [M. M. Ip, Cancer Res 40: 2188 (1980)]; and diethylstilbesterol induced renal tumors in hamsters [A. H. Dodge, Eur J Cancer Clin Oncol 13: 1377 (1977)].

In humans, tamoxifen has been used with varying degrees of success to treat a variety of estrogen receptor positive carcinomas such as breast cancer, endometrial carcinoma, prostate carcinoma, ovarian carcinoma, renal carcinoma, melanoma, colorectal tumors, desmoid tumors, pancreatic carcinoma, and pituitary tumors. [B. J. Furr, Pharmac Ther 25: 127 (1984)].

DESCRIPTION OF THE EMBODIMENTS

This invention provides a method of treating estrogen receptor positive carcinoma in a mammal in need thereof which comprises administering an antineoplastic amount of 17(α-dihydroequilin or a mammalian metabolic conjugate thereof orally, parenterally, transdermally, topically, rectally, intravaginally, intranasally, or intrabronchially. In particular, the compounds of this invention are useful in preventing the growth of estrogen receptor positive carcinomas, reducing the size of estrogen receptor positive carcinomas, or eradicating estrogen receptor positive carcinomas in a mammal bearing an estrogen receptor positive carcinoma. As such, the compounds of this invention are useful in treating estrogen receptor positive carcinomas such as carcinomas of the breast, uterus, ovary, fallopian tube, cervix, vagina, liver, pituitary, central nervous system, hypothalamus, bone, skin, kidney, urethra, prostate, and the like.

The mammalian metabolic conjugates are sulfates and glucuronides of 17(α-dihydroequilin, where 17(α-dihydroequilin can either be in the form of a mono- or di-conjugate. In addition, it is also contemplated that any derivative of 17(α-dihydro-equilin that forms 17(α-dihydroequilin or a conjugate thereof in vivo will also be useful in treating estrogen receptor positive carcinomas.

17α-Dihydroequilin is commercially available and the conjugates are either commercially available or can be prepared by using standard chemical methodology.

The abitlity of the compounds of this invention to prevent the growth of estrogen receptor positive carcinomas, reduce the size of estrogen receptor positive carcinomas, and eradicate estrogen receptor positive carcinomas was established in one in vitro and one in vitro standard pharmacological test procedure. The procedures used and results obtained are briefly described below. Tamoxifen was also evaluated in both test procedures for the purpose of comparison.

In the in vitro standard pharmacological test procedure, 17α-dihydroequilin was evaluated as a representative compound in MCF-7 (estrogen receptor positive) and NMA-231 (estrogen receptor negative) human breast cancer cell lines to determine the effect of the compounds of this invention on cell proliferation as measured by the percent of the cells present in the $G_1$, S, and $G_2/M$ phases of the cell cycle. Briefly, the cell lines were plated in T-25 tissue culture flasks at an initial density of between 50,000 and 100,000 cells/flask and incubated for a period of 24 hours in phenol-red free IMEM medium supplemented with dextran-coated-charcoal stripped fetal bovine serum (10%), glutamine (5 mg/mL) and gentamycin sulfate (2 mg/mL). The cells were then treated with either 17(α-dihydroequilin or tamoxifen alone, or with either 17(α-dihydroequilin or tamoxifen in combination with $E_2$. After 24 hours of incubation, the test media was removed and the cells were harvested for flow cytometric analysis of DNA content according to the method of Vindelov [Cytometry 3: 323(1983)]. The following results were obtained.

As expected, the administration of $E_2$ to the estrogen receptor positive MCF-7 cell line caused cell proliferation as evidenced by the shift of cells from the G1 phase of the cell cycle to the S phase; this shift was not observed in response to administration of $E_2$ to the estrogen receptor negative MDA-231 cell line indicating a lack of proliferation. Similar responses to endogenous $E_2$ occur in mammals with estrogen receptor positive and negative carcinomas, respectively. Treatment of the MCF-7 cell line with 17α-dihydroequilin (0.1 µM) alone did not cause a shift of cells from the resting $G_1$ phase to the proliferative S phase indicating that 17α-dihydroequilin lacked estrogenic activity. A similar result was observed with tarnoxifen (0.1 µM).

The following table shows the percent of cells in the $G_1$, S, and $G_2$/M phases of the cell cycle when the two cell lines were treated with a combination of $E_2$ (1 nM) and 17α-dihydroequilin (0.1 nM) or tamoxifen (0.1 nM).

| Treatment | % $G_1$ | % S | % $G_2$/M |
|---|---|---|---|
| MCF-7 | | | |
| Control | 45 | 45 | 9 |
| $E_2$ | 29 | 66 | 5 |
| 17α-dihydroequilin + $E_2$ | 42 | 42 | 15 |
| Tamoxifen + $E_2$ | 40 | 46 | 14 |
| MDA-231 | | | |
| Control | 34 | 52 | 14 |
| $E_2$ | 38 | 45 | 17 |
| 17α-dihydroequilin + $E_2$ | 26 | 60 | 13 |
| Tamoxifen + $E_2$ | 28 | 58 | 14 |

The results of this standard pharmacological test procedure showed that 17α-dihydroequilin prevented the $E_2$ induced proliferation of the estrogen receptor positive MCF-7 human breast cancer cell line as evidenced by the cells not being shifted from the resting $G_1$ phase to the proliferative S phase. A similar result was obtained with tamoxifen.

The ability of the compounds of this invention to cause a reduction in estrogen receptor positive carcinoma size was demonstrated with 17(α-dihydroequilin sulfate as a representative compound in an in vivo standard pharmacological procedure using DMBA induced mammary carcinoma in rats. Tamoxifen was also evaluated for the purpose of comparison. Briefly, Sprague-Dawley female rats between 50–55 days of age were treated with DMBA (20 mg) in peanut oil (2 mL). The development of tumors were measured by calipers, and tumor volumes calculated. When at least one tumor per rat reached 2 cm in diameter, the rat was selected for one of the treatment groups. Rats were treated either with vehicle (control), 17α-dihydroequilin sulfate, or tamoxifen. In addition, one group of rats were ovariectomized after tumor development and then treated with vehicle. The animals were treated for a 4 week period. Tumor volumes were measured weekly. The following table shows the results that were obtained as expressed in percent change in tumor size from week 0, when treatment was initiated.

| PERCENT CHANGE OF TUMOR SIZE FROM WEEK 0 | | | | |
|---|---|---|---|---|
| Treatment (daily dose) | Week 1 | Week 2 | Week 3 | Week 4 |
| Control | 22.9 | 52.4 | 53.0 | 107.4 |
| Ovariectomized | −8.0 | −3.3 | 30.7 | 34.0 |
| 17(α-DHEQ-S (0.5 mg/kg)* | 47.2 | 75.9 | 59.4 | 111.6 |
| 17α-DHEQ-S (5.0 mg/kg) | −18.2 | −21.2 | −8.2 | 3.1 |
| 17(α-DHEQ-S (25.0 mg/kg) | −49.7 | + | −51.2 | −46.7 |
| Tamoxifen (2.0 mg/kg) | + | −18.7 | −28.5 | −20.1 |

*17(α-DHEQ-S = 17α-Dihydroequilin sulfate.
+Not measured.

As expected, the estrogen receptor positive DMBA induced breast carcinomas developed slower in the ovariectomized rats than in the control rats, because of diminished endogenous estrogen (particularly $E_2$) levels. The results of this in vivo standard pharmacological test procedure demonstrate that the compounds of this invention cause a reduction in the size of estrogen receptor positive carcinomas. Treatment with tamoxifen also caused a reduction in tumor size.

In summary, the results of these standard pharmacological test procedures show that treatment of estrogen receptor positive carcinomas with the compounds of this invention caused a reduction of cell proliferation by inhibiting progression beyond the $G_1$ phase of the cell cycle and caused a reduction in tumor size. As the cells are held in the $G_1$ cell phase, the inventors conclude that continued treatment of an estrogen receptor positive carcinoma using an antineoplastic amount of the compounds of this invention will cause eradication of the carcinoma, because the cells are thus incapable of undergoing DNA and protein synthesis which is necessary to maintain cellular survival.

As such the compounds of this invention are useful in treating estrogen receptor positive carcinomas of a variety of tissue such as breast, uterus, ovary, fallopian tube, cervix, vagina, liver, pituitary, central nervous system, hypothalamus, bone, skin, kidney, urethra, prostate, and the like.

When the compounds of this invention are employed in the treatment of estrogen receptor positive carcinomas, they can be formulated into oral dosage forms such as tablets, capsules and the like. The compounds can be administered alone or by combining them with conventional carriers, such as magnesium carbonate, microcrystalline cellulose, talc, sugar, lactose, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds of this invention may also be injected parenterally, in which case they are used in the form of a sterile solution containing other solutes, for example, enough saline or glucose to make the solution isotonic.

The compounds of this invention also may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The compounds of this invention may be employed as a solution, cream, or lotion by formulation with pharmaceutically acceptable vehicles which may be administered to an affected area.

The dosage requirements vary with the particular compositions employed, the route of administration, the severity of the symptoms presented and the particular subject being treated. Based on the results obtained in the standard pharmacological test procedures, projected daily dosages of active compound would be 0.09 $\mu$g/kg–1 mg/kg, preferably between 0.1–75 mg/kg, and more preferably between 5–50 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. In general, the compounds of this invention are most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method of treating an estrogen receptor positive carcinoma selected from the group consisting of estrogen receptor positive carcinoma of the breast, uterus, ovary, fallopian tube, cervix, vagina, liver, pituitary, central nervous system, hypothalamus, bone, skin, kidney, urethra, and prostate in a mammal in need thereof which comprises administering to said mammal an effective antineoplastic amount of 17α-dihydroequilin or a sulfate or glucuronide conjugate thereof orally, parenterally, transdermally, topically, rectally, intravaginally, intranasally, or intrabronchially; wherein said 17α-dihydroequilin or a sulfate or glucuronide conjugate thereof is in substantially purified form.

2. The method according to claim 1 in which the administered compound is 17α-dihydroequilin.

3. The method according to claim 1 in which the administered compound is 17α-dihydroequilin sulfate.

4. The method according to claim 1 in which the estrogen receptor positive carcinoma is of the breast.

5. The method according to claim 2 in which the estrogen receptor positive carcinoma is of the breast.

6. The method according to claim 3 in which the estrogen positive carcinoma is of the breast.

7. A method of preventing the growth of an estrogen receptor positive carcinoma, reducing the size of an estrogen receptor positive carcinoma, or eradicating an estrogen receptor positive carcinoma in a mammal bearing an estrogen receptor positive carcinoma which comprises administering to said mammal an effective antineoplastic amount of 17α-dihydroequilin or a sulfate or glucuronide conjugate thereof orally, parenterally, transdermally, topically, rectally, intravaginally, intranasally, or intrabronchially; wherein the estrogen receptor positive carcinoma is selected from the group of an estrogen receptor positive carcinoma of the breast, uterus, ovary, fallopian tube, cervix, vagina, liver, pituitary, central nervous system, hypothalamus, bone, skin, kidney, urethra, and prostate; and wherein said 17α-dihydroequilin or a sulfate or glucuronide conjugate thereof is in substantially purified form.

8. The method according to claim 7 in which the administered compound is 17α-dihydroequilin.

9. The method according to claim 7 in which the administered compound is 17α-dihydroequilin sulfate.

10. The method according to claim 7 in which the estrogen receptor positive carcinoma is of the breast.

11. The method according to claim 8 in which the estrogen receptor positive carcinoma is of the breast.

12. The method according to claim 9 in which the estrogen receptor positive carcinoma is of the breast.

13. The method according to claim 1 in which said 17 α-dihydroequilin or sulfate or glucuronide conjugate thereof is combined with one or more pharmaceutically acceptable carriers.

14. The method according to claim 7 in which said 17 α-dihydroequilin or sulfate or glucuronide conjugate thereof is combined with one or more pharmaceutically acceptable carriers.

15. The method according to claim 13 in which the administered daily dose of 17α-dihydroequilin or a sulfate or glucuronide conjugate thereof is from 0.09 $\mu$g/kg to 100 mg/kg.

16. The method according to claim 15 in which the administered daily dose of 17α-dihydroequilin or a sulfate or glucuronide conjugate thereof is from 5 mg/kg to 50 mg/kg.

17. The method according to claim 14 in which the administered daily dose of 17α-dihydroequilin or a sulfate or glucuronide conjugate thereof is from 0.09 $\mu$g/kg to 100 mg/kg.

18. The method according to claim 17 in which the administered daily dose of 17α-dihydroequilin or a sulfate or glucuronide conjugate thereof is from 5 mg/kg to 50 mg/kg.

* * * * *